United States Patent
Imai

Patent Number: 5,151,524
Date of Patent: Sep. 29, 1992

[54] PROCESS FOR PREPARING IMIDAZOLIDINE-2,5-DIONE DERIVATIVE

[75] Inventor: Tetuya Imai, Naruto, Japan

[73] Assignee: Otsuka Kagaku Kabushiki Kaisha, Osaka, Japan

[21] Appl. No.: 553,519

[22] Filed: Jul. 18, 1990

[30] Foreign Application Priority Data

Jul. 19, 1989 [JP] Japan .................................. 1-187064
Feb. 27, 1990 [JP] Japan .................................. 2-48030

[51] Int. Cl.$^5$ .......................................... C07D 235/30
[52] U.S. Cl. ................................................... 548/307
[58] Field of Search ....................................... 548/307

[56] References Cited

U.S. PATENT DOCUMENTS 4,578,107  3/1986  Imai ................................... 548/307

Primary Examiner—Mary C. Lee
Assistant Examiner—Robert C. Whittenbaugh
Attorney, Agent, or Firm—Armstrong & Kubovcik

[57] ABSTRACT

A process for preparing an imidazolidine-2,5-dione derivative of the formula

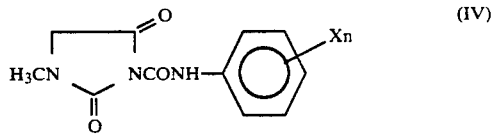

(IV)

includes reacting a phenyl isocyanate compound of the formula

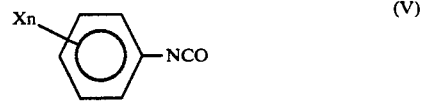

(V)

with methylhydantoin of the formula

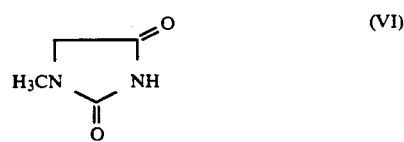

(VI)

in the presence of a basic catalyst, wherein X is a halogen atom, lower alkyl, lower alkoxyl, lower haloalkyl, nitro cyano or alkoxycarbonyl, and n is an interger of 0 or 1 to 4. A second process for preparing an imidazolidine-2,5-dione derivative of formula IV includes reacting phosgene or trichloromethyl chloroformate with methylhydantoin of formula VI in the presence of a dehydrogen chloride agent, and further reacting the resulting product with an aniline derivative of formula VII

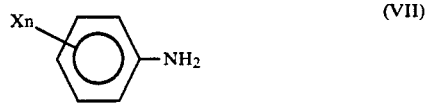

(VII)

in the presence of a dehydrogen chloride agent, wherein X is same as above.

3 Claims, No Drawings

PROCESS FOR PREPARING IMIDAZOLIDINE-2,5-DIONE DERIVATIVE

The present invention relates to a process for preparing an imidazolidine-2,5-dione derivative which is simple and high in yield, the derivative being an intermediate of imidazolidine-2-one derivative which is an agriculturally useful herbicide.

It is known that the following imidazolidine-2-one derivative is high in herbicidal activity and useful as a herbicide,

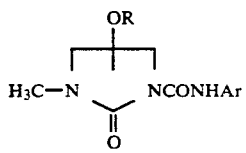

wherein R is hydrogen atom, lower alkyl, lower alkoxy lower alkyl or lower alkoxycarbonyl lower alkyl, Ar is phenyl which may have, as a substituent, halogen atom, nitro, lower alkyl, lower alkoxyl or lower haloalkyl. For example, U.S. Pat. No. 4,578,107 discloses that the derivatives are markedly effective in controlling weeds such as *Eclipta prostrata, Amaranthus retroflexus, Aeschynomeme indica, Alopecurus aequalis* var. *amurensis, Polygonum Hydropiper, Artemisia princeps, Erigeron sumatrensis, Rumex japonicus, Lindernia pyxidaria, Rotela indica, Echinochloa Crus-galli, Digitaria adscendens Eleusine indica, Cyperus microiria*, etc. Therefore, the present compounds are useful in preventing or controlling weeds which are harmful to agricultural crop plants such as those of citrus, apples, soy beans, corns, mulberries, tea, paddyrice, etc. or which impair the surrounding scenic beauty.

In order to use effectively such a useful compound, it is important to produce the same easily at an industrial scale. The above U.S. patent discloses a process for producing the imidazolidine-2-one derivative of the above formula [I], in which imidazolidine-2,4-dione derivative of the formula [II] or imidazolidine-2,5-dione derivative of the formula [III] is reduced and further alkylated to obtain the desired compound,

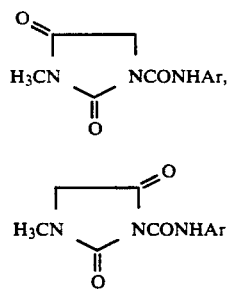

wherein Ar is as defined above.

In the above, the starting compounds [II] and [III] can be prepared by a usual manner in which 1- or 3-methylhydantoin is reacted by heat with phenyl isocyanate generally with or without use of a solvent. The compound [II], an intermediate, is prepared in a high yield, for example, in 80% or more in reference example of the above U.S. patent. On the other hand, the compound [III], an intermediate, is not obtained in a sufficient yield by the above method, for example, in about 30% at most in reference example of the above U.S. patent. Further, in case of using a phenyl isocyanate having a substituent in ortho position as a starting compound, the yield is particularly low and such starting compound can not be used for industrial production.

An object of the invention is to provide a process for preparing an imidazolidine-2,5-dione derivative of the formula [III] which is simple and high in yield and purity, the derivative being an intermediate of a herbicide compound.

The above and other objects of the invention will become apparent from the following description.

The present invention provides two kinds of methods of preparing an imidazolidine-2,5-dione derivative.

The present invention firstly provides a process for preparing an imidazolidine-2,5-dione derivative of the formula

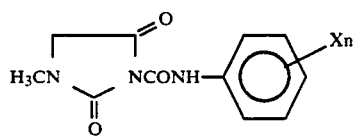

which comprises reacting a phenyl isocyanate compound of the formula

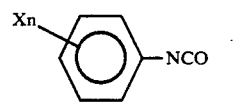

with methylhydantoin of the formula

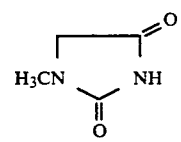

in the presence of a basic catalyst, wherein X is halogen atom, lower alkyl, lower alkoxyl, lower haloalkyl, nitro, cyano or alkoxycarbonyl, n is an integer of 0 or 1 to 4.

The above first process is described below in detail. The reaction is conducted preferably in a solvent. The solvent may be any of those which do not cause adverse effect on the reaction and includes benzene, toluene, xylene or like aromatic solvent; dichloromethane, chloroform, dichloroethane or like halogenated hydrocarbon, ethyl ether, diisopropyl ether, dibutyl ether, dioxane or like ether.

Examples of basic catalysts used in the present invention are triethylamine, tributylamine, dimethylaniline, diethylaniline, hexamethylenetetramine or like tertiary amine, and preferably used is triethylamine. The amount of the catalyst used is usually 0.5 to 0.01 mole, preferably 0.2 to 0.05 mole per mole of methylhydantoin of the formula [VI]. The proportion of methylhydantoin of the formula [VI] and phenyl isocyanate of the formula [V] is not particularly limited and is selected from a wide range, and the latter is used usually in an amount of 0.5 to 3 moles, preferably 1 to 2 moles per mole of the former. The reaction proceeds insufficiently when the reaction temperature is too low and is apt to accompany side reactions when the reaction temperature is too high. Preferably the reaction is conducted in the range of 0° to 80° C. The reaction time is about 3 to 10 hours, although it is somewhat different depending on the kind of the phenyl isocyanate compound.

The present invention also provides a process for preparing an imidazolidine-2,5-dione derivative of the formula

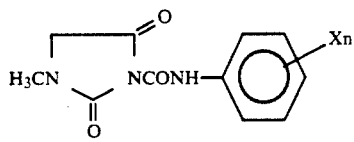
(IV)

which comprises reacting phosgene or trichloromethyl chloroformate with methylhydantoin of the formula

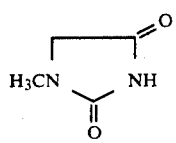
(VI)

in the presence of a dehydrogen chloride agent, and further reacting the resulting product with an aniline derivative of the formula

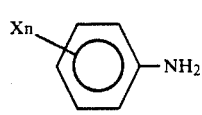
(VII)

in the presence of a dehydrogen chloride agent, wherein X is same as above.

The above second process is described below in detail. The reaction is conducted preferably in a solvent. The solvent may be any of those which are known in the art and do not cause adverse effect on the reaction and includes benzene, toluene, xylene or like aromatic hydrocarbon; dichloromethane, dichloroethane, chloroform or like halogenated hydrocarbon, diethyl ether, diisopropyl ether, dibutyl ether, dioxane or like ether; ethyl acetate or like ester.

The above second process of the present invention comprises a first step of reacting phosgene or trichloromethyl chloroformate with methylhydantoin and a second step of further reacting the resulting product with the aniline derivative. It is preferable to conduct these reactions in the same reaction vessel in the above solvent without isolating the intermediate.

A dehydrogen chloride agent is used in both of the first and second steps of the present second process. Examples of the dehydrogen chloride agents are triethylamine, tributylamine, dimethylaniline, diethylaniline or like tertiary amine; pyridine, picoline, lutidine or like pyridine derivative, and preferably used is pyridine.

In the first step, phosgene or trichloromethyl chloroformate is used usually in an amount of 0.1 to 2 moles, preferably 0.25 to 1.5 moles per mole of methylhydantoin. The dehydrogen chloride agent is used in an amount which corresponds to an amount of phosgene or trichloromethyl chloroformate. When introducing the starting materials into a reaction vessel, it is preferable to introduce gaseous phosgene or to add dropwise through a funnel liquid trichloromethyl chloroformate, to a solvent having dissolved therein methylhydantoin and the dehydrogen chloride agent, with cooling. The reaction temperature is preferably about −10° to 50° C., and reaction time is about 5 to 20 hours.

In the second step of the present second process, the reaction product of the first step is, without isolation, reacted with the aniline derivative of the formula [VII] in the presence of the dehydrogen chloride agent. The aniline derivative is used usually in an amount of 0.5 to 2 moles, preferably 0.7 to 1.5 moles per mole of methylhydantoin. The dehydrogen chloride agent is preferably used in an equivalent mole of the aniline derivative. The reaction temperature is preferably about −10° to 50° C., and reaction time is about 5 to 20 hours.

The desired compound of the present invention thus obtained is easily isolated and purified by a usual purification method such as washing with a solvent, recrystallization or the like.

According to the present invention, the desired compound [IV] can be obtained in a high yield. The compound is high in purity without a specific purification and thus the present process is advantageous industrially.

The invention will be described in detail with reference to examples and reference examples.

EXAMPLE 1

Preparation of 3-methylimidazoline-2,5-dione-1-carboxy(2-fluoroanilide)

Into 300-ml four-necked flask were placed 4.6 g (0.04 mole) of methylhydantoin, 50 ml of dichloroethane and 0.5 ml of triethylamine. To the mixture was added dropwise at room temperature with stirring 5.5 g (0.04 mole) of 2-fluorophenyl isocyanate in 3 ml of dichloroethane for 5 minutes. The mixture was stirred at room temperature for 5 hours, and the resulting crude crystals were collected by filtration. The crude crystals were washed with water and with ethanol and then dried at 60° C. under reduced pressure for 2 hours, giving 8.5 g (yield 84.2%) of the above desired compound in the form of colorless crystal.

Melting point: 166.6° C.

NMR: δ(CDCl$_3$) 3.00(3H), 3.90(2H), 6.85–7.20(3H), 8.15(1H), 10.20(1H)

EXAMPLE 2

Preparation of 3-methylimidazoline-2,5-dione-1-carboxy(3,4-dichloroanilide)

Into 300-ml four-necked flask were placed 3.4 g (0.03 mole) of methylhydantoin, 40 ml of dichloroethane and 0.4 ml of triethylamine. To the mixture was added dropwise at room temperature with stirring 5.6 g (0.03 mole) of 3,4-dichlorophenyl isocyanate in 3 ml of dichloroethane for 5 minutes. The mixture was stirred at room temperature for 4 hours, and the resulting crystals were collected by filtration. The crude crystals were washed with water and with ethanol and then dried at 60° C. under reduced pressure for 2 hours, giving 8.0 g (yield 88.9%) of the above desired compound in the form of colorless crystal.

Melting point: 179.9° C.

NMR: δ(CDCl$_3$) 2.98(3H), 3.88(2H), 7.20(2H), 7.50(1H), 10.05(1H)

EXAMPLES 3 to 18
The compounds of Examples 3 to 18 were prepared in the same manner as in Example 1. Table 1 shows properties, yield and NMR data of the obtained compounds.
TABLE 1
| No. | Y | m.p. (°C.) | yield (%) | NMR δ(CDCl₃) |
|---|---|---|---|---|
| 3 | phenyl | 134.9 | 90.4 | 2.98(3H), 3.87(2H), 6.90~7.52(5H), 9.93(1H) |
| 4 | 2-Cl-phenyl | 166.6 | 83.9 | 3.00(3H), 3.90(2H), 6.85~7.40(3H), 8.20(1H), 10.25(1H) |
| 5 | 2-Br-phenyl | 173.7 | 84.1 | 3.00(3H), 3.90(2H), 7.90(1H), 7.10(1H), 7.40(1H), 8.12(1H), 10.20(1H) |
| 6 | 3-Cl-phenyl | 151.7 | 89.2 | 2.98(3H), 3.88(2H), 6.90~7.30(3H), 7.50(1H), 10.00(1H) |
| 7 | 4-Cl-phenyl | 151.6 | 89.7 | 2.98(3H), 3.88(2H), 7.13(2H), 7.40(2H), 10.03(1H) |
| 8 | 2-CH₃-phenyl | 143.7 | 85.3 | 2.23(3H), 3.00(3H), 3.88(2H), 6.85~7.20(3H), 7.90(1H), 9.90(1H) |
| 9 | 4-CH₃-phenyl | 164.8 | 91.6 | 2.23(3H), 3.00(3H), 3.90(2H), 6.94(2H), 7.22(2H), 10.20(1H) |
| 10 | 2-C₂H₅-phenyl | 122.4 | 83.5 | 1.20(3H), 2.63(2H), 3.00(3H), 3.98(2H), 6.90~7.20(3H), 7.85(1H), 9.90(1H) |
| 11 | 2-OCH₃-phenyl | 141.9 | 85.5 | 3.00(3H), 3.80(3H), 3.85(2H), 6.75~7.05(3H), 8.15(1H), 10.10(1H) |

TABLE 1-continued $$\underset{\text{H}_3\text{CN}}{\overset{\text{O}}{\diagdown}} \underset{\text{O}}{\overset{}{\diagdown}} \text{NCNH-Y}$$

| No. | Y | m.p. (°C.) | yield (%) | NMR δ(CDCl₃) |
|---|---|---|---|---|
| 12 | 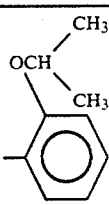 | 137.0 | 83.2 | 1.35(6H), 2.98(3H), 3.87(2H), 4.50(1H), 6.70~6.95(3H), 8.15(1H), 10.12(1H) |
| 13 | 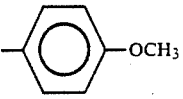 | 134.8 | 90.8 | 2.98(3H), 3.70(3H), 3.98(2H), 6.72(2H), 7.30(2H), 9.75(1H) |
| 14 | 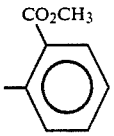 | 138.3 | 82.5 | 3.05(3H), 3.70(3H), 3.90(2H), 6.95~7.40(3H), 8.10(1H), 10.15(1H) |
| 15 | 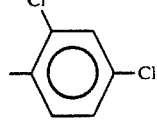 | 154.1 | 84.3 | 3.00(3H), 3.90(2H), 7.20(2H), 8.15(1H), 10.25(1H) |
| 16 | 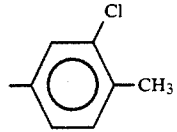 | 139.7 | 88.5 | 2.26(3H), 2.98(3H), 3.88(2H), 7.07(2H), 7.45(1H), 9.90(1H) |
| 17 | 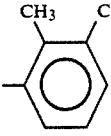 | 156.7 | 83.2 | 2.30(3H), 3.00(3H), 3.90(2H), 7.05(2H), 7.75(1H), 9.95(1H) |
| 18 | 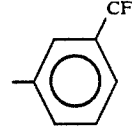 | 102.8 | 89.2 | 2.96(3H), 3.89(2H), 6.90~7.40(3H), 7.52(1H), 10.00(1H) |

REFERENCE EXAMPLE 1

Preparation of 3-methyl-5-hydroxyimidazolidine-2-one-1-carboxy-(2-fluoroanilide)

In 50 ml of methanol was dispersed 7.53 g (0.03 mole) of 3-methylimidazoline-2,5-dione-1-carboxy-(2-fluoroanilide). After cooled to 10° C., 1.2 g (0.03 mole) of sodium borohydride was added to the dispersion with stirring. The mixture was stirred for 30 minutes and then further stirred at room temperature for 2 hours. After completion of the reaction, the reaction mixture was concentrated and water was added to the residue to precipitate crystals. The crystals were filtered and recrystallized from ethanol to obtain 6.92 g (yield 91.2%) of white crystals.

Melting point: 139.2° C.
NMR: δ(CDCl₃) 2.75(3H), 3.13(1H), 3.42(1H), 4.56(1H), 5.76(1H), 6.75–7.15(3H), 7.95(1H), 10.20(1H)

REFERENCE EXAMPLES 2 TO 12

The compounds of Reference Examples 2 to 12 were prepared in the same manner as in Reference Example 1.

TABLE 2

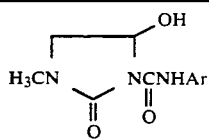

| No. | Ar | m.p. (°C.) |
|---|---|---|
| 2 | phenyl | 178.5 |
| 3 | 2-Cl-phenyl | 169 |
| 4 | 3-Cl-phenyl | 160.5 |
| 5 | 2,3-diCl-phenyl | 201 |
| 6 | 2-Br-phenyl | 149 |
| 7 | 2-CH₃-phenyl | 174 |
| 8 | 3-CH₃-phenyl | 164.5 |
| 9 | 4-CH₃-phenyl | 197 |
| 10 | 2-OCH₃-phenyl | 175 |
| 11 | 3-OCH₃-phenyl | 155 |

TABLE 2-continued

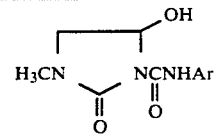

| No. | Ar | m.p. (°C.) |
|---|---|---|
| 12 | 2-CF₃-phenyl | 148 |

EXAMPLE 19

Preparation of 3-methylimidazoline-2,5-dione-1-carboxy(2-fluoroanilide)

Into 300-ml four-necked flask were placed 5.7 g (0.05 mole) of methylhydantoin, 4.0 g (0.05 mole) of pyridine, 49 ml of dichloroethane and 1 ml of ethyl acetate. To the mixture placed in an ice bath was added dropwise with stirring 3.1 ml (0.025 mole) of trichloromethyl chloroformate. After stirred at room temperature for 10 hours, the mixture was cooled again and thereto were added 5.6 g (0.05 mole) of 2-fluoroaniline and 4.0 g (0.05 mole) of pyridine. The mixture was stirred at room temperature for 7 hours, and the resulting crude crystals were collected by filtration. The crude crystals were washed with water and with ethanol and then dried under reduced pressure, giving 7.6 g of the above desired compound in the form of colorless crystal.

Yield: 60.5%

Melting point: 166° C.

NMR: $\delta$(CDCl₃) 3.00(3H), 3.90(2H), 6.85–7.20(3H), 8.15(1H), 10.20(1H)

EXAMPLE 20

Preparation of 3-methylimidazoline-2,5-dione-1-carboxy(2-fluoroanilide)

The above desired compound (5.4 g, melting point 166° C.) was obtained in the same manner as in Example 19 except that 5 g of gaseous phosgene was used in place of trichloromethyl chloroformate.

Yield: 43.0%

EXAMPLES 21 TO 36

Each of the compounds listed in Table 3 below was prepared in the same manner as in Example 19 or 20 with use of a corresponding starting material. Table 3 also shows yields when both of phosgene and trichloromethyl chloroformate are used as a starting material.

TABLE 3

| Ex. No. | Xn | m.p. (°C.) | yield (%) (1) | yield (%) (2) |
|---|---|---|---|---|
| 21 | H | 134 | 73.5 | 60.5 |

TABLE 3-continued

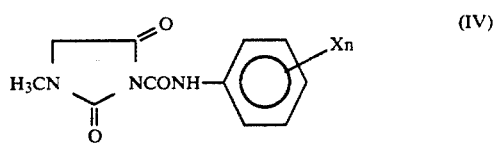

| Ex. No. | Xn | m.p. (°C.) | yield (%) (1) | yield (%) (2) |
|---|---|---|---|---|
| 22 | 2-Cl | 166 | 58.4 | 42.7 |
| 23 | 2-Br | 173 | 55.3 | 40.5 |
| 24 | 3-Cl | 151 | 71.0 | 55.5 |
| 25 | 4-Cl | 151 | 72.5 | 53.6 |
| 26 | 2-CH$_3$ | 143 | 54.5 | 40.2 |
| 27 | 4-CH$_3$ | 164 | 73.7 | 60.9 |
| 28 | 2-C$_2$H$_5$ | 122 | 50.5 | 40.0 |
| 29 | 2-OCH$_3$ | 141 | 51.0 | 42.5 |
| 30 | 2-OCH(CH$_3$)$_2$ | 137 | 49.0 | 38.5 |
| 31 | 4-OCH$_3$ | 134 | 73.0 | 55.8 |
| 32 | 2-COOC$_2$H$_5$ | 138 | 46.3 | 37.0 |
| 33 | 2,4-Cl$_2$ | 154 | 56.5 | 45.5 |
| 34 | 3-Cl, 4-CH$_3$ | 139 | 70.4 | 58.5 |
| 35 | 2-CH$_3$, 3-Cl | 156 | 50.5 | 49.6 |
| 36 | 3-CF$_3$ | 102 | 70.5 | 63.4 |

Note:
(1) yield when phosgene is used as a starting material
(2) yield when trichloromethyl chloroformate is used as a starting material

TEST USING A PLANT

Test Example 1 (Postemergence Test)

A Wagner's pot (1/2000 are) was filled with sterilized alluvial soil, and seeds of the plants listed in Table 4 were sown or transplanted. The compound of Reference Examples was dissolved in acetone and thereto was added Tween 80 in an amount of 10%. The mixture was diluted with water to apply in an amount of 50 g ai/10a, and the dilution was sprinkled so that allover the stems and leaves become wet uniformly when each of the plants grew to an approximately constant height (2- to 3-leaf stage). Three weeks after the treatment, a herbicidal effect was examined on each of the plants. The results were given in Table 4. The herbicidal activity was evaluated with an unaided eye and expressed in terms of index relative to non-treated one according to the following criteria.

| (Index) | (Herbicidal activity) |
|---|---|
| 0 | no effect |
| 1 | 1 to 24% kill |
| 2 | 25 to 49% kill |
| 3 | 50 to 74% kill |
| 4 | 75 to 90% kill |
| 5 | complete kill |

TABLE 4

| Compound | A | B | C | D | E | F | G | H |
|---|---|---|---|---|---|---|---|---|
| 1 | 5 | 5 | 5 | 5 | 5 | 5 | 3 | 5 |
| 2 | 5 | 5 | 4 | 5 | 5 | 5 | 2 | 5 |
| 3 | 5 | 5 | 5 | 5 | 5 | 5 | 3 | 5 |
| 4 | 5 | 5 | 3 | 5 | 5 | 5 | 2 | 5 |
| 5 | 5 | 5 | 3 | 5 | 5 | 5 | 2 | 5 |
| 6 | 5 | 5 | 5 | 5 | 5 | 5 | 3 | 5 |
| 7 | 5 | 5 | 5 | 5 | 5 | 5 | 3 | 5 |
| 8 | 5 | 5 | 4 | 5 | 5 | 5 | 2 | 5 |
| 9 | 5 | 5 | 3 | 5 | 5 | 5 | 2 | 5 |
| 10 | 5 | 5 | 4 | 5 | 5 | 5 | 2 | 5 |
| 11 | 5 | 5 | 4 | 5 | 5 | 5 | 2 | 5 |

TABLE 4-continued

| Compound | A | B | C | D | E | F | G | H |
|---|---|---|---|---|---|---|---|---|
| 12 | 5 | 5 | 4 | 5 | 5 | 5 | 3 | 5 |

In the above Table, the plants A to H are as follows.
A *Amaranthus retroflexus*,
B *Aeschynomene indica*,
C *Echinochloa Crus-galli*,
D *Raphanus sativus*,
E *Fagopyrum esculentum*,
F *Pharbitis Nil var. japonica*
G *Triticum*,
H *Eclipta prostrata*

Test EXAMPLE 2 (preemergence test)

A Wagner's pot (1/2000 are) was filled with sterilized alluvial soil, and seeds of the plants listed in Table 5 were sown and covered with the soil in about 0.5 to 1 cm. The compound of Reference Examples was dissolved in acetone and thereto was added Tween 80 in an amount of 10%. The mixture was diluted with water to apply in an amount of 50 g ai/10a, and the dilution was sprinkled so that the surface of the soil become wet uniformly. Three weeks after the treatment, a herbicidal effect was examined on each of the plants. The results were given in Table 5. The herbicidal activity was evaluated in the same manner as in Test Example 1.

TABLE 5

| Compound | A | B | C | D | E | F | G |
|---|---|---|---|---|---|---|---|
| 1 | 5 | 5 | 5 | 5 | 5 | 5 | 5 |
| 2 | 5 | 5 | 5 | 5 | 5 | 5 | 5 |
| 6 | 5 | 5 | 5 | 5 | 5 | 5 | 5 |

The plants A to G are same as in Table 4.

I claim:

1. A process for preparing an imidazolidine-2,5-dione derivative of the formula

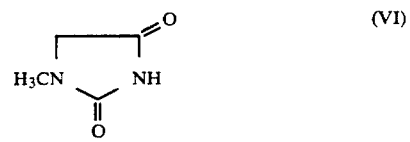

(IV)

which comprises reacting phosgene or trichloromethyl chloroformate with methylhydantoin of the formula (VI)

(structure as shown)

in the presence of a dehydrogen chloride agent, and further reacting the resulting product with an aniline derivative of the formula

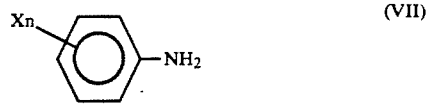

(VII)

in the presence of a dehydrogen chloride agent, wherein X is halogen atom, lower alkyl, lower alkoxyl, lower haloalkyl, nitro, cyano or alkoxycarbonyl, n is an integer of 0 or 1 to 4.

2. The process of claim 1, wherein said dehydrogen chloride agent is selected from the group consisting of triethylamine, tributylamine, dimethylaniline, diethylaniline, pyridine, picoline and lutidine.

3. A process as defined in claim 2, wherein the dehydrogen chloride agent is pyridine.

* * * * *